United States Patent
Ito et al.

(10) Patent No.: US 11,213,186 B2
(45) Date of Patent: Jan. 4, 2022

(54) ENDOSCOPE APPARATUS AND IMAGE PROCESSING APPARATUS

(71) Applicant: OLYMPUS CORPORATION, Tokyo (JP)

(72) Inventors: Tadashi Ito, Hachioji (JP); Sho Nakamura, Kawasaki (JP)

(73) Assignee: OLYMPUS CORPORATION, Tokyo (JP)

(*) Notice: Subject to any disclaimer, the term of this patent is extended or adjusted under 35 U.S.C. 154(b) by 110 days.

(21) Appl. No.: 16/654,090

(22) Filed: Oct. 16, 2019

(65) Prior Publication Data

US 2020/0037849 A1 Feb. 6, 2020

Related U.S. Application Data

(63) Continuation of application No. PCT/JP2017/015587, filed on Apr. 18, 2017.

(51) Int. Cl.
*A61B 1/00* (2006.01)
*A61B 1/05* (2006.01)
(Continued)

(52) U.S. Cl.
CPC ...... *A61B 1/00009* (2013.01); *A61B 1/00025* (2013.01); *A61B 1/00071* (2013.01);
(Continued)

(58) Field of Classification Search
CPC ............ A61B 1/00004; A61B 1/00025; A61B 1/00027; A61B 1/00029; A61B 1/00032;
(Continued)

(56) References Cited

U.S. PATENT DOCUMENTS

2004/0090189 A1* 5/2004 Yoneda .................. H05B 45/14
  315/291
2007/0038030 A1* 2/2007 Kaneko ................ A61B 1/0684
  600/180
(Continued)

FOREIGN PATENT DOCUMENTS

EP  3101460 A1  12/2016
JP  2003-333873 A  11/2003
(Continued)

OTHER PUBLICATIONS

International Search Report dated Jul. 25, 2017 issued in PCT/JP2017/015587.

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

The endoscope apparatus includes an endoscope and a video processor. The endoscope apparatus has a voice coil motor provided in a distal end portion of an insertion portion of the endoscope and having a coil with a resistance component, and a signal wire inserted into the insertion portion and connected to both ends of the coil, detects at least one value of a current supplied to the signal wire and a voltage applied to the signal wire, calculates power consumption of the coil from the at least one value detected and resistance value information of the resistance component, and executes a predetermined process based on the calculated power consumption of the coil and power consumption threshold information.

20 Claims, 8 Drawing Sheets

(51) Int. Cl.
*A61B 1/06* (2006.01)
*G06T 7/00* (2017.01)

(52) U.S. Cl.
CPC ............ *A61B 1/051* (2013.01); *G06T 7/0012* (2013.01); *A61B 1/0684* (2013.01)

(58) Field of Classification Search
CPC ............ A61B 1/00034; A61B 1/00036; A61B 1/00062; A61B 1/00188; A61B 1/0676; A61B 1/128; A61B 1/041; A61M 2205/60; A61M 2205/6054; A61M 2205/6063; A61M 2205/6072; A61M 2205/6081; G01R 21/06; G06F 1/06; H04N 5/232411; H04N 5/23241
See application file for complete search history.

(56) References Cited

U.S. PATENT DOCUMENTS

| | | | | |
|---|---|---|---|---|
| 2007/0244366 | A1* | 10/2007 | Murata | A61B 1/00059 600/175 |
| 2008/0027284 | A1* | 1/2008 | Suda | A61B 1/00055 600/134 |
| 2008/0076087 | A1* | 3/2008 | Horie | A61C 1/088 433/29 |
| 2009/0203965 | A1* | 8/2009 | Fujiyama | A61B 1/00096 600/130 |
| 2009/0284588 | A1* | 11/2009 | Matsui | A61B 1/00059 348/65 |
| 2012/0004509 | A1* | 1/2012 | deLucia | H05B 45/37 600/199 |
| 2012/0178992 | A1* | 7/2012 | Fujimoto | H04N 7/183 600/109 |
| 2013/0030248 | A1* | 1/2013 | Matsumaru | A61B 1/00027 600/110 |
| 2013/0197308 | A1* | 8/2013 | Sugawara | G02B 23/2476 600/118 |
| 2013/0265403 | A1* | 10/2013 | Okawa | A61B 1/045 348/76 |
| 2014/0275783 | A1* | 9/2014 | Blanquart | A61B 1/00006 600/112 |
| 2015/0280550 | A1* | 10/2015 | Minakuchi | G02B 23/2484 348/65 |
| 2016/0037079 | A1* | 2/2016 | Gocho | H04N 5/232 348/240.3 |
| 2016/0334599 | A1 | 11/2016 | Kono et al. | |
| 2016/0353540 | A1* | 12/2016 | Merkt | H05B 45/10 |

FOREIGN PATENT DOCUMENTS

| | | |
|---|---|---|
| JP | 2007-229262 A | 9/2007 |
| JP | 2012-065850 A | 4/2012 |
| JP | 2015-125094 A | 7/2015 |
| JP | 2015125094 A * | 7/2015 |
| JP | 2015-141278 A | 8/2015 |
| WO | WO 2015/114867 A1 | 8/2015 |

* cited by examiner

ENDOSCOPE APPARATUS AND IMAGE PROCESSING APPARATUS

CROSS REFERENCE TO RELATED APPLICATION

This application is a continuation application of PCT/JP2017/015587 filed on Apr. 18, 2017, the entire contents of which are incorporated herein by this reference.

BACKGROUND OF THE INVENTION

1. Field of the Invention

The present invention relates to an endoscope apparatus and an image processing apparatus, and specifically relates to an endoscope apparatus and an image processing apparatus in which a temperature of a distal end portion of an insertion portion can be maintained and managed without providing a temperature sensor in the distal end portion.

2. Description of the Related Art

Endoscope apparatuses are widely used in a medical field and an industrial field. Endoscope apparatuses have an insertion portion that is inserted into an object, and irradiate the object with illumination light from a distal end portion so that an examiner can observe the inside of the object by looking at an endoscope image based on light reflected from the object.

Various components are provided inside the distal end portion of the insertion portion. The distal end portion of the insertion portion has a temperature that is increased due to, for example, heat generated by a light emitting device. Not only the light emitting device but also electronic components such as an image pickup device are provided inside the distal end portion and these electronic components also cause a temperature increase in the distal end portion.

For example, Japanese Patent Application Laid-Open Publication No. 2007-229262 proposes an endoscope apparatus provided with a temperature sensor inside a distal end portion of an insertion portion for reduction of heat generation in the distal end portion, in which irradiation by a light emitting diode is stopped or reduced when a detected temperature is a predetermined value or more.

SUMMARY OF THE INVENTION

An endoscope apparatus according to one embodiment of the present invention includes an endoscope, a device arranged in a distal end portion of an insertion portion of the endoscope and having a resistance component, a signal wire inserted into the insertion portion and connected to both ends of the device, and a processor composed of hardware, wherein the processor detects at least one value of a current supplied to the signal wire and a voltage applied to the signal wire, calculates power consumption of the device from the at least one value detected and resistance value information of the resistance component, and executes a predetermined process based on the calculated power consumption of the device and power consumption threshold information.

An image processing apparatus according to one embodiment of the present invention includes a processor composed of hardware, the image processing apparatus allowing connection of an endoscope, wherein the processor detects at least one value of a current supplied to a signal wire connected to both ends of a device provided in a distal end portion of an insertion portion of the endoscope and having a resistance component, and a voltage applied to the signal wire, calculates power consumption of the device from the at least one value detected and resistance value information of the resistance component, and executes a predetermined process based on the calculated power consumption of the device and power consumption threshold information.

DETAILED DESCRIPTION OF THE PREFERRED EMBODIMENTS

Embodiments of the present inventions are explained below with the use of the drawings.

First Embodiment (Entire Configuration)

Figure 1:
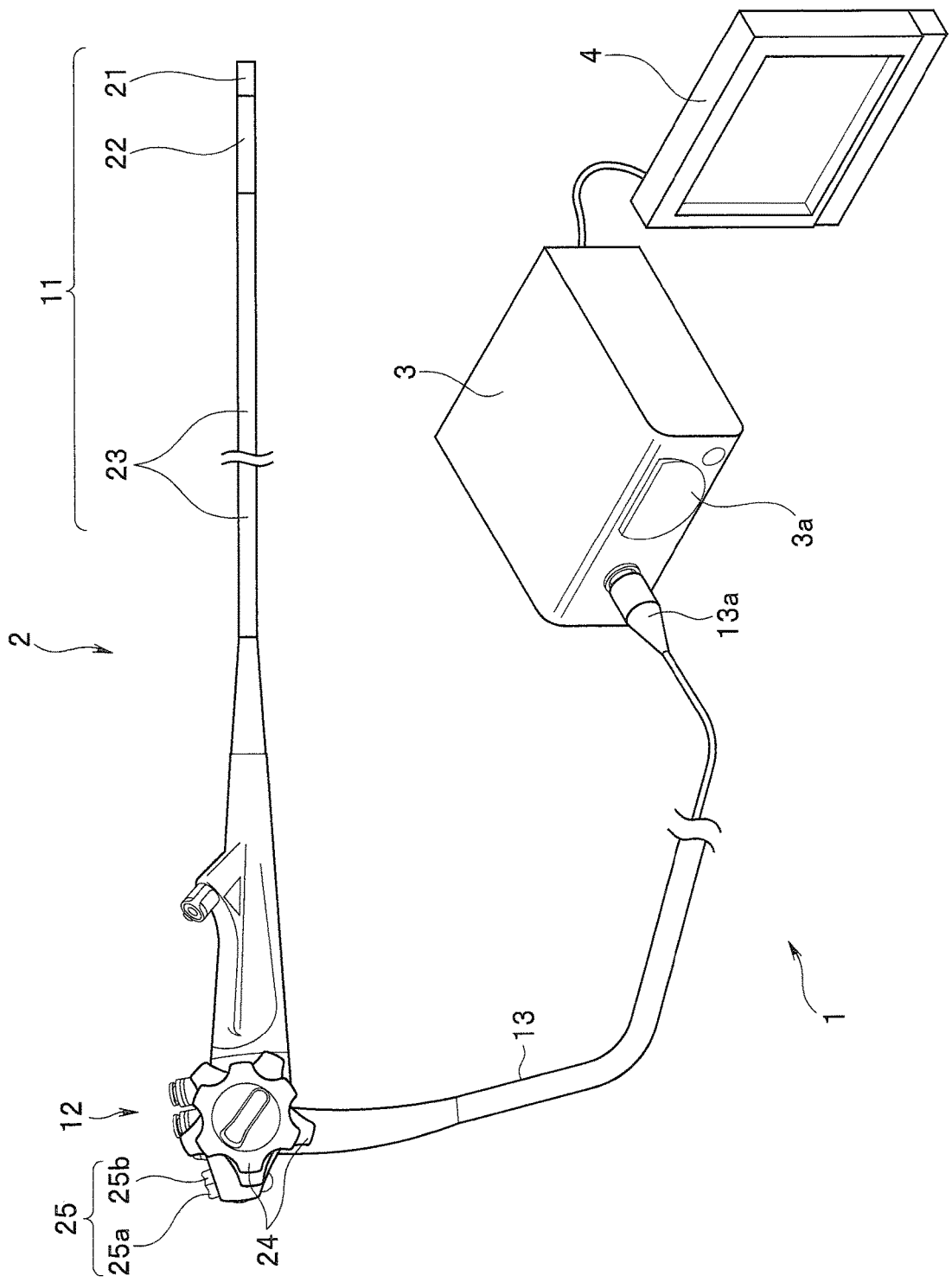
FIG. 1 is a configuration diagram showing a configuration of an endoscope apparatus 1 according to a first embodiment of the present invention.

FIG. 1 is a configuration diagram showing a configuration of an endoscope apparatus according to the present embodiment. As shown in FIG. 1, an endoscope apparatus 1 according to the present embodiment is configured to have an endoscope 2 and a video processor 3 to which the endoscope 2 is connected. A monitor 4 is connected to the video processor 3.

The video processor 3 serving as an image processing apparatus has a connector and the endoscope 2 is a main body portion that is connectable to the connector. A user who conducts an endoscopic examination can select any endoscope 2 from a plurality of endoscopes according to the examination and connect the selected endoscope 2 to the video processor 3.

The endoscope 2 is an electronic endoscope that has an elongated insertion portion 11, an operation portion 12 connected to a proximal end of the insertion portion 11, and a universal cable 13 extending from the operation portion 12.

The insertion portion 11 of the endoscope 2 has a rigid distal end portion 21 at a tip end and a bendable bending portion 22 provided adjacent to the distal end portion 21, and further includes a long flexible tube portion 23 disposed to a proximal end side of the bending portion 22.

Figure 2:
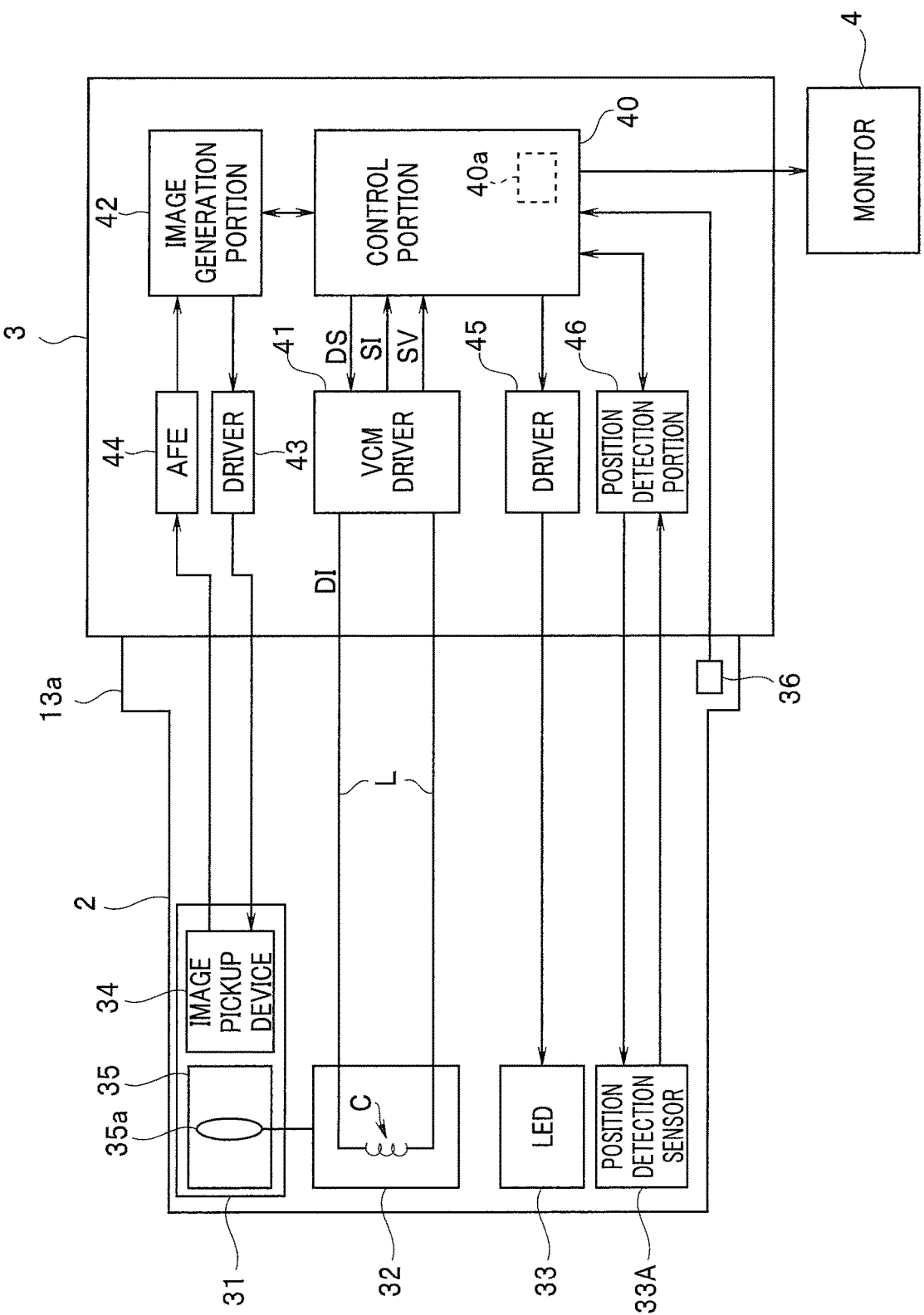
FIG. 2 is a block diagram showing a configuration of the endoscope apparatus 1 according to the first embodiment of the present invention.

The distal end portion 21 incorporates an image pickup device 34 and an image pickup optical system 35 (see FIG. 2). The distal end portion 21 is provided with an observation window (not shown) and light from an object passes through the observation window and the image pickup optical system 35 to be made incident on a light receiving surface of the image pickup device 34. The image pickup optical system 35 is an observation optical system having a zoom mechanism. An image pickup signal obtained by the image pickup device 34 is supplied to the video processor 3 via signal wires inserted into the insertion portion 11, the operation portion 12 and the universal cable 13.

Note that the image pickup optical system 35 serving herein as an observation optical system having a zoom mechanism with variable image pickup magnifications may also be an observation optical system having a mechanism to drive a lens instead of the zoom mechanism. Namely, the image pickup optical system 35 should have at least a lens driving mechanism.

Note that various signal wires are also inserted into the universal cable 13 in order to transmit an actuator driving signal or the like to be described later.

The distal end portion 21 is further provided with an illumination window (not shown). A light emitting diode 33 (see FIG. 2) is disposed to a rear side of the illumination window to emit illumination light.

A user of the endoscope apparatus 1 is allowed to bend the bending portion 22 in vertical and horizontal directions by operating two bending knobs 24 provided in the operation portion 12.

The operation portion 12 is provided with various operating tools such as a release button, and a zoom operating tool 25 for driving a zoom lens to be described later.

The zoom operating tool 25 has a button 25a configured to cause zooming to a tele side of the zoom mechanism, and a button 25b configured to cause zooming to a wide side of the zoom mechanism. When a user presses the button 25a, during the pressing of the button, a zoom lens 35a (see FIG. 2) is moved for zooming to the tele side. When a user stops pressing the button 25a, the zoom lens 35a stops in a zoom position at that time. Similarly, when a user presses the button 25b, during the pressing of the button, the zoom lens 35a is moved for zooming to the wide side. When a user stops pressing the button 25b, the zoom lens 35a stops in a zoom position at that time. Therefore, a user is allowed to observe an object in a desired zoom position or zoom amount by the operation of pressing the buttons 25a, 25b.

Note that the zoom operating tool 25 provided herein as the two buttons 25a, 25b arranged in the operation portion 12 of the endoscope 2 may also be any of other operating tools such as a foot switch connected to the video processor 3.

At a tip end of the universal cable 13 extending from the operation portion 12 (i.e., at a proximal end of the endoscope 2), a connector 13a is provided. The connector 13a can be detachably attached to a connector of the video processor 3.

The video processor 3 incorporates a control portion 40 (see FIG. 2) configured to control the endoscope apparatus 1 as a whole. A user can perform various operations by using various buttons of the operation portion 12 and an operation panel 3a, etc. of the video processor 3. The control portion 40 executes programs according to various functions in response to operation by a user.

The video processor 3 is a processor configured to receive an image pickup signal from the endoscope 2 and generate an endoscope image as an object image. An image signal of the endoscope image is outputted to the monitor 4 to display the endoscope image on the monitor 4.

The endoscope 2 has a zoom function and a user operates the zoom operating tool 25 so as to display an endoscope image on the monitor 4 at an angle of view as desired by the user. The video processor 3 drives an actuator of the endoscope 2 in response to operation of the zoom operating tool 25 by a user.

As stated above, the endoscope apparatus 1 is composed of an endoscope 2 having an observation optical system that has a lens driving mechanism, and the video processor 3 serving as a processor to which the endoscope 2 is connected.

FIG. 2 is a block diagram showing a configuration of the endoscope apparatus 1.

The endoscope 2 includes an image pickup portion 31, a voice coil motor 32 serving as an actuator, the light emitting diode (hereinafter referred to as LED) 33, and a position detection sensor 33A. The image pickup portion 31, the voice coil motor (VCM) 32, the LED 33 and the position detection sensor 33A are provided inside the distal end portion 21 of the insertion portion 11.

The image pickup portion 31 has the image pickup device 34 such as a CCD image sensor and the image pickup optical system 35. The image pickup optical system 35 is a zoom optical system as stated above and includes the zoom lens 35a that is a movable lens. The image pickup device 34 receives, on the light receiving surface, light from an object image via the image pickup optical system 35 and photoelectrically converts the received light to output as an image pickup signal.

The voice coil motor 32 is an electric actuator provided in the endoscope 2 and configured to drive a lens associated with a lens driving mechanism of the zoom optical system. Herein, the voice coil motor 32 can move the zoom lens 35a in an optical axis direction of the image pickup optical system 35. The voice coil motor 32 is a magnetic actuator composed of a coil C and a magnet and driven by a drive current DI. When the drive current DI is supplied to the voice coil motor 32 and the voice coil motor 32 is driven, the coil C generates heat.

The zoom lens 35a is connected to a movable portion of the voice coil motor 32 and the movable portion is moved relative to a fixed portion inside the voice coil motor 32, whereby the zoom lens 35a can be moved by the voice coil motor 32 in the optical axis direction of the image pickup optical system 35.

As stated above, the actuator provided in the distal end portion 21 is a voice coil motor that has at least one magnet and at least one coil C and is capable of moving the movable portion relative to the fixed portion.

The position detection sensor 33A detects a position of the zoom lens 35a or the movable portion of the voice coil motor in the optical axis direction. The position detection sensor 33A is, for example, a hall device.

The LED 33 is a light emitting device configured to emit light serving as illumination light, and emits illumination light from the illumination window (not shown) of the distal end portion 21 to an object.

Note that in place of the LED 33 used herein as an illumination portion, a light source apparatus may be provided separately to expose illumination light onto an object by guiding light from the light source apparatus to the distal end portion 21 with the use of a light guide composed of an optical fiber bundle and emitting light from a tip end surface of the light guide in the distal end portion 21.

The endoscope 2 includes a memory 36. The memory 36 is provided herein inside the connector 13a of the universal cable 13.

The memory 36 is a rewritable nonvolatile memory or, for example, a flash memory. Predetermined information is stored in the memory 36 in advance. The predetermined information includes resistance value ratio information Rat and power consumption threshold information pTH. Details of the information are described later.

When the endoscope 2 is connected to the video processor 3, predetermined information recorded in the memory 36 is read by the video processor 3.

Note that predetermined information may also be stored in a storage apparatus such as a ROM in the video processor 3. In this case, model information of the endoscope 2 is stored in the memory 36 of the endoscope 2 and a plurality of predetermined information corresponding to models are stored in a ROM or the like of the video processor 3. The video processor 3 can read, from a ROM or the like, predetermined information corresponding to a model of the endoscope 2 that is connected to the video processor 3.

The video processor 3 serving as a main body portion of the endoscope apparatus 1 includes the control portion 40, a voice coil motor driver (hereinafter referred to as the VCM driver) 41, an image generation portion 42, a driver 43, an analog front end circuit (hereinafter referred to as AFE) 44, a driver 45, and a position detection portion 46.

The control portion 40 makes a control to drive the voice coil motor 32 in addition to perform various processes corresponding to the entire operation of the endoscope apparatus 1, generation of various images and various functions. The control portion 40 includes a central processing unit (CPU), a ROM, a RAM and the like not shown and temperature maintenance processes to be described later are performed by executing a program stored in the ROM. Note that FIG. 2 shows only a plurality of blocks relevant to the control to drive the voice coil motor 32.

The VCM driver 41 generates, based on a drive instruction signal DS sent from the control portion 40, the drive current DI supplied to the voice coil motor 32, and outputs the drive current DI to the voice coil motor 32 via two signal wires L. Further, the VCM driver 41 outputs, to the control portion 40, a current value signal SI corresponding to a current supplied to the voice coil motor 32, and a voltage value signal SV corresponding to a voltage at an output end of the VCM driver 41.

Although it is not shown in FIG. 2, when a user presses the aforementioned button 25a or 25b, a zoom instruction signal is outputted from the zoom operating tool 25 to the control portion 40. The control portion 40 outputs, based on the zoom instruction signal, the drive instruction signal DS to drive the voice coil motor 32, whereby the zoom lens 35a is moved. Owing to the movement of the zoom lens 35a, a zoom position of the image pickup optical system 35 changes and, as a result, a size of an object image displayed on the monitor 4 is changed.

Note that the VCM driver 41 provided herein in the video processor 3 may also be provided in the endoscope 2. For example, the VCM driver 41 may also be provided inside the connector 13a of the endoscope 2.

Figure 3:
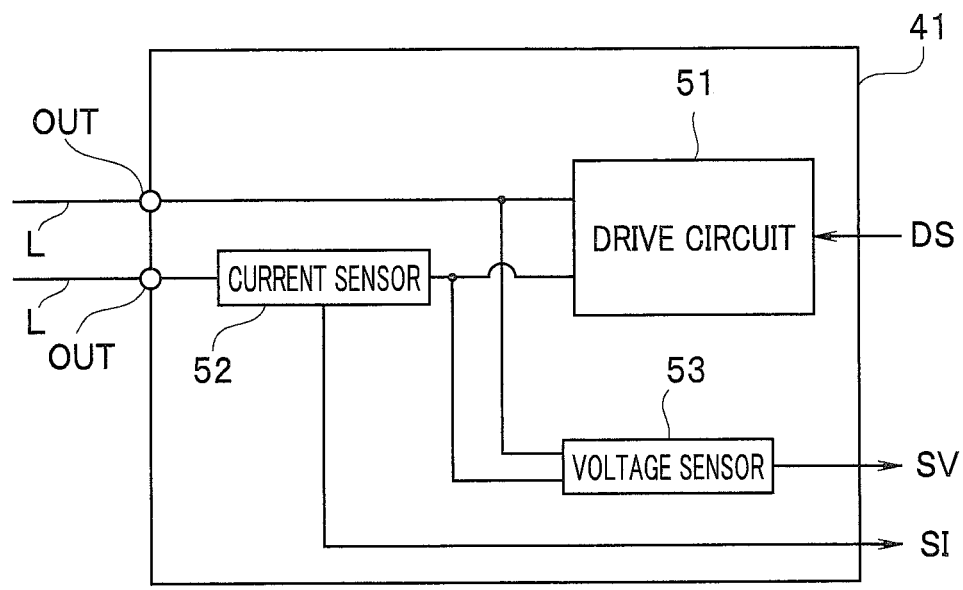
FIG. 3 is a block diagram showing a configuration of a VCM driver 41 according to the first embodiment of the present invention.

FIG. 3 is a block diagram showing a configuration of the VCM driver 41. The VCM driver 41 includes a drive circuit 51, a current sensor 52 and a voltage sensor 53. The drive circuit 51 receives the drive instruction signal DS from the control portion 40 and outputs the drive current DI that is a drive signal corresponding to the drive instruction signal DS.

The current sensor 52 detects the magnitude of a current of the drive signal DI flowing through the signal wires L by which the VCM driver 41 and the voice coil motor 32 are connected, and outputs the current value signal SI indicating a current value to the control portion 40.

The voltage sensor 53 detects the magnitude of a voltage between the two output ends OUT connected to the signal wires L by which the VCM driver 41 and the voice coil motor 32 are connected, and outputs the voltage value signal SV indicating a voltage value to the control portion 40.

Figure 4:
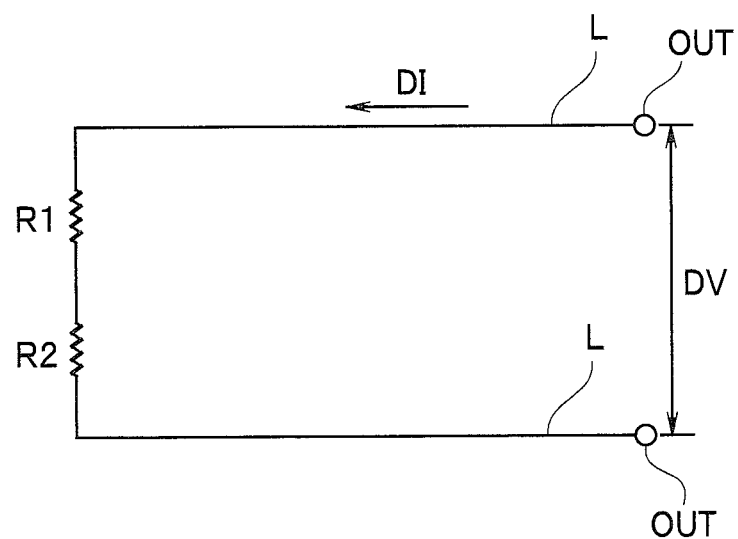
FIG. 4 is a wiring diagram to explain a resistance value of two signal wires L and a resistance value of a voice coil motor 32 to be viewed from output ends OUT of the VCM driver 41 according to the first embodiment of the present invention.

FIG. 4 is a wiring diagram to explain a resistance value of the two signal wires L and a resistance value of the voice coil motor 32 to be viewed from the output ends OUT of the VCM driver 41. The two signal wires L viewed from the output ends OUT of the VCM driver 41 include two resistance components.

Each of the signal wires L has a length of, for example, 4 m and a conductor resistance R1 corresponding to the length. The conductor resistance R1 has a resistance value r1. The voice coil motor 32 has an internal resistance R2 and the internal resistance R2 has a resistance value r2. A resistance value of the coil C of the voice coil motor 32 corresponds to the resistance value r2 of the internal resistance R2. Namely, the coil C of the voice coil motor 32 serving as an actuator is a device provided in the distal end portion 21 of the insertion portion 11 and having a resistance component of the resistance value r2. The two signal wires L are inserted into the insertion portion 11 and connected to both ends of the coil C as the device.

The sum of the resistance values r1, r2 corresponds to a composite resistance value R included in the signal wires L viewed from the output ends OUT.

Therefore, a current value of the drive signal DI outputted from the output end OUT of the VCM driver 41 and a voltage between the output ends OUT vary according to the resistance values r1, r2. For example, the resistance value r1 is 8 ohms and the resistance value r2 is 24 ohms.

The current sensor 52 and the voltage sensor 53 constitute a signal detection portion to detect a current supplied to the two signal wires L and a voltage applied to the two signal wires L, respectively.

The endoscope 2 of various kinds may be connected to the video processor 3, in which the resistance values r1, r2 vary depending on each model of the endoscope 2. Further, the resistance values r1, r2 may be set to a constant design value but vary owing to individual differences.

Returning to FIG. 2, the image generation portion 42 includes a circuit configured to output, under the control of the control portion 40, a drive signal to drive the driver 43 for the image pickup portion 31 and to receive an image signal from the AFE 44 to generate an endoscope image. The image generation portion 42 generates an endoscope image by applying various processes to the image signal from the AFE 44 and outputs the endoscope image to the control portion 40. The control portion 40 outputs an image signal of the endoscope image to the monitor 4.

The driver 43 generates various drive signals including a horizontal synchronizing signal and a vertical synchronizing signal to drive the image pickup device 34 and outputs the various drive signals to the image pickup device 34.

The AFE 44 includes an analog-digital converter or the like to convert an image pickup signal from the image pickup portion 31 into a digital signal and outputs an image pickup signal subjected to a noise removal process or other processes to the image generation portion 42.

The driver 45 generates, under the control of the control portion 40, a drive signal to drive the LED 33 and outputs the drive signal to the LED 33.

The video processor 3 drives the LED 33 to irradiate an object with illumination light and generates, based on an image pickup signal from the image pickup portion 31 that receives light reflected from the object, an image signal to output to the monitor 4 and causes an endoscope image to be displayed on a display screen of the monitor 4.

The position detection portion 46 generates, under the control of the control portion 40, a drive signal to drive the position detection sensor 36 and outputs the drive signal to the position detection sensor 36. The position detection portion 46 outputs, based on a position detection signal received from the position detection sensor 36, a position detection value to the control portion 40.

Next, a relationship between power consumption of the voice coil motor 32 and a temperature of the distal end portion 21 is explained.

When the image pickup portion 31, the voice coil motor 32 and the LED 33 are driven, heat is generated. Herein, a case is explained on the assumption that maximum heat is generated by driving the voice coil motor 32 and a temperature of the distal end portion 21 is maintained and managed based on a heat generation state of the voice coil motor 32.

When the drive current DI is supplied to the voice coil motor 32, the distal end portion 21 generates heat due to power consumption in the resistance value r2 of the voice coil motor 32.

Figure 5:
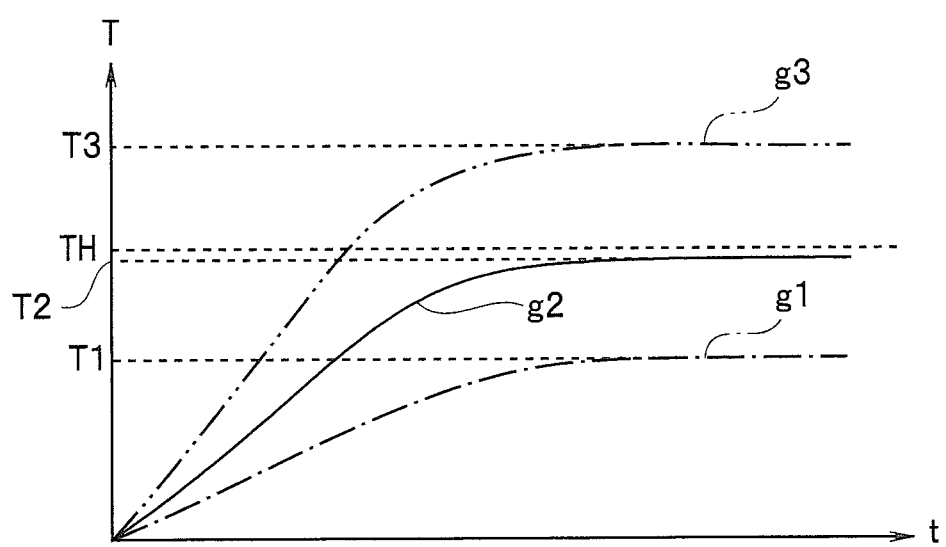
FIG. 5 provides schematic graphs showing temperature changes in a distal end portion 21 corresponding to power consumption in an internal resistance R2 of the voice coil motor 32 and with the lapse of time, according to the first embodiment of the present invention.

FIG. 5 shows schematic graphs indicating temperature changes in the distal end portion 21 corresponding to power consumption in the internal resistance R2 of the voice coil motor 32 and with the lapse of time.

The graphs shown in FIG. 5 are plotted from data obtained through, for example, experiment or simulation. The graphs of FIG. 5 are created in such a manner that the drive current DI is changed for each model of the endoscope 2 and temperature of the distal end portion 21 corresponding to power consumption of the internal resistance R2 are obtained through measurement or simulation so as to be plotted.

The distal end portion 21 incorporates the image pickup device 34, the voice coil motor 32 and the LED 33. As stated above, on the assumption herein that power consumption of the voice coil motor 32 is greater than power consumption of each of the image pickup device 34 and the LED 33 and the most influential to the temperature of the distal end portion 21, a temperature of distal end portion 21 is estimated based on power consumption of the voice coil motor 32.

A heat capacity and heat dissipation characteristics of the distal end portion 21 are determined by a structure and a material, etc. of the distal end portion 21 and a use environment of the endoscope. Due to a design value and an allowable error of each component to constitute the endoscope 2 and production variations of the endoscope 2, a power consumption threshold varies depending on each endoscope.

Therefore, by measuring temperature changes in the distal end portion 21 when power consumption of the voice coil motor 32 is changed through experiment or simulation, data as shown in FIG. 5 is obtained for each endoscope. From a relationship between power consumption of the voice coil motor 32 and a temperature of the distal end portion 21 thus obtained through experiment, etc., a value of power consumption of the voice coil motor 32 obtained when the distal end portion 21 reaches the maximum allowable temperature is determined. The determined value is stored as a power consumption threshold for each model of the endoscope 2 in the memory 36 of the endoscope 2 in advance. In other words, information of different power consumption threshold for respective models of the endoscope 2 is stored in the memory 36 of the endoscope 2.

Note that when individual differences of the endoscope 2 of the same model are within an allowable range, model information of the endoscope may be stored in the memory 36 of the endoscope 2 and information of power consumption thresholds for respective models of the endoscope may be stored in a nonvolatile memory 40a (shown by broken line in FIG. 2) of the control portion 40. When the endoscope 2 is connected to the video processor 3, the control portion 40 may read model information of the endoscope 2 from the memory 36 and read a power consumption threshold by referring to the memory 40a based on the model information.

In FIG. 5, a graph g1 shown by a one-dot dashed line indicates a temperature change in the distal end portion 21 when the drive current DI having a first current value is made to flow through the signal wires L and power consumption of the internal resistance R2 of the voice coil motor 32 is p1. The graph g1 shows upward movement with the lapse of time and no change from certain time so that the distal end portion 21 is stabilized at a temperature T1.

A graph g2 shown by a solid line indicates a temperature change in the distal end portion 21 when the drive current DI having a second current value that is greater than the first current value is made to flow through the signal wires L and power consumption of the internal resistance R2 is p2. The graph g2 also shows upward movement with the lapse of time and no change from certain time so that the distal end portion 21 is stabilized at a temperature T2.

A graph g3 shown by a two-dot dashed line indicates a temperature change in the distal end portion 21 when the drive current DI having a third current value that is greater than the second current value is made to flow through the signal wires L and power consumption of the internal resistance R2 is p3. The graph g3 also shows upward movement with the lapse of time and no change from certain time so that the distal end portion 21 is stabilized at a temperature T3.

Although FIG. 5 shows only three graphs, a plurality of graphs may be obtained through experiment or simulation by causing a plurality of the drive currents DI having mutually different current values to flow through the signal wires L.

Herein, when a temperature of the distal end portion 21 rises too high, it causes, for example, an increased noise amount included in an image pickup signal of the image pickup device 34 and therefore prevents achieving a predetermined image quality level. In other words, when a temperature of the distal end portion 21 rises too high, it prevents maintaining a predetermined performance level of the endoscope 2.

In the case of FIG. 5, assuming the highest temperature at which such a predetermined performance level can be maintained is TH, the temperature of the distal end portion 21 can be maintained below TH when power consumption of the internal resistance R2 is P2 or less. Therefore, the p2 is stored as a power consumption threshold pTH in the memory 36 in advance.

Information of a ratio between the resistance value r1 of the signal wires L and the resistance value r2 of the voice coil motor 32 is also stored in the memory 36 in advance. The ratio information is stored in the memory 36 because even if there is a change in a use environment of the endoscope apparatus 1, a ratio (r2/r1) of the resistance value r2 of the voice coil motor 32 to the resistance value r1 of the signal wires L is substantially constant.

Note that information of the resistance values r1, r2 may be stored as predetermined information in the memory 36 in place of the ratio information so as to calculate a ratio from the resistance values r1, r2 by the control portion 40.

Since the insertion portion 11 of the endoscope 2 is inserted into the body of an object in use, the resistance value r1 of the signal wires L and the resistance value r2 of the voice coil motor 32 are actually measured in the same environment as the use environment as stated above.

For example, because the distal end portion 21 of the insertion portion 11 is inside the body of an object in endoscopy, the ratio (r2/r1) of the resistance value r2 of the voice coil motor 32 to the resistance value r1 of the signal wires L is actually measured when the distal end portion 21 is at, for example 40 degrees and portions other than the distal end portion 21 are at a room temperature that is, for example, 25 degrees, and the ratio information Rat is stored in the memory 36. The ratio information Rat is resistance value information of a resistance component of the coil C.

However, if there is a temperature difference between the distal end portion 21 and portions other than the distal end portion but ratio variations are within an allowable range, the ratio information Rat obtained by actually measuring the ratio (r2/r1) of the resistance value r2 to the resistance value r1 when the distal end portion 21 and portions other than the distal end portion 21 are at the same temperature may be stored in the memory 36.

A design value may also be used without actual measurement of the resistance values r1, r2. In this case, a design value set at, for example, 25 degrees may be used as r1 and a design value set at, for example, 40 degrees may be used as r2.

Effect

Next, temperature maintenance processes applied to the distal end portion 21 in the endoscope apparatus 1 are explained.

Figure 6:
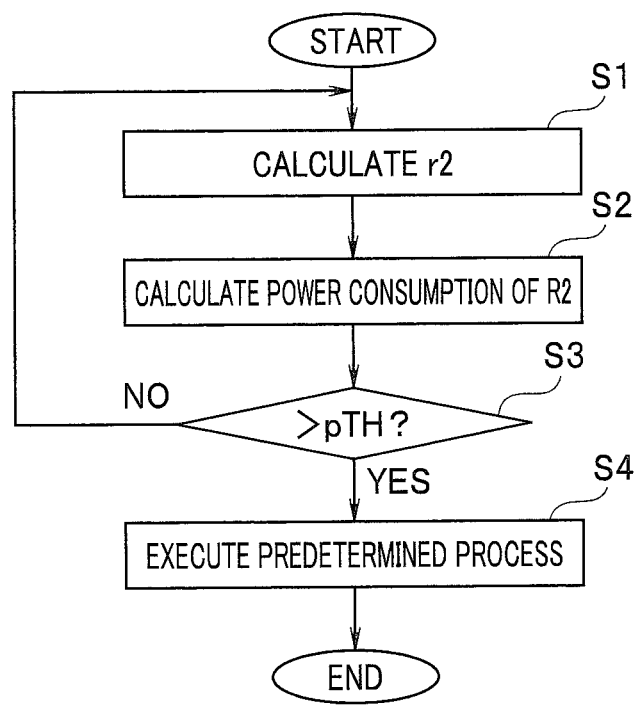
FIG. 6 is a flowchart showing an example of a flow of temperature maintenance processes in the distal end portion 21 of the endoscope apparatus 1 according to the first embodiment of the present invention.

FIG. 6 is a flowchart showing an example of a flow of temperature maintenance processes applied to the distal end portion 21 in the endoscope apparatus 1. A process program in FIG. 6 is stored in the ROM and read by the CPU in the control portion 40.

The control portion 40 first calculates the resistance value r2 of the internal resistance R2 as a point resistance in the voice coil motor 32 (step (hereinafter referred to as S) 1).

The control portion 40 can calculate power consumption of the internal resistance R2 of the voice coil motor 32 from the current value signal SI and the voltage value signal SV sent from the VCM driver 41 and the ratio information Rat stored in the memory 36.

Initially, an equation (1) below is used to calculate the composite resistance value R from the current value I of the current value signal SI and the voltage value V of the voltage value signal SV.

$$R=V/I \qquad (1)$$

Because a resistance (i.e., conductor resistance) of the signal wires L has the resistance value r1 and a resistance (i.e., internal resistance) of the coil of the voice coil motor 32 has the resistance value r2, the composite resistance value R is expressed by an equation (2) below.

$$R=r1+r2 \qquad (2)$$

As stated above, the internal resistance R2 as a point resistance is a coil resistance that constitutes the voice coil motor 32.

Additionally, from the ratio information Rat, a relationship between the resistance value r1 and the resistance value r2 is expressed by an equation (3) below.

$$r1=r2/\text{Rat} \qquad (3)$$

From the equation (2) and the equation (3) above, the resistance value r2 is expressed by an equation (4) below.

$$r2=R-r1=R-(r2/(\text{Rat})) \qquad (4)$$

From the equation (4), an equation (5) below is obtained.

$$r2=(R\times\text{Rat})/(\text{Rat}+1) \qquad (5)$$

Namely, from the calculated R and the ratio information Rat, the resistance value r2 is calculated.

After S2, the control portion 40 calculates power consumption of the internal resistance R2 of the voice coil motor 32 (S2). Power consumption of the internal resistance R2 of the voice coil motor 32 is expressed by an equation (6) below.

$$PWr2=I^2\times r2 \qquad (6)$$

Hence, from r2 calculated by the equation (5) and the current value I detected by the current sensor 52, power consumption of the internal resistance R2 of the voice coil motor 32 is calculated.

As stated above, the process at S2 constitutes a power consumption calculation part to calculate power consumption of the coil C by using the current value I and the voltage value V detected by the current sensor 52 and the voltage sensor 53 serving as a signal detection portion and the ratio information Rat serving as resistance value information of the resistance component of the coil C.

Note that when model information of the endoscope 2 is stored in the memory 36 as stated above, resistance value information of the resistance component of the coil C is obtained from the ROM based on the model information read from the memory 36 and power consumption is calculated by using the obtained resistance value information at S2.

Then, the control portion 40 determines whether or not power consumption calculated at S2 exceeds the threshold pTH read from the memory 36 (S3).

If power consumption calculated at S2 does not exceed the threshold pTH (S3: NO), the process returns to S1.

If power consumption calculated at S2 exceeds the threshold pTH (S3: YES), the control portion 40 executes a predetermined process (S4).

In the state where power consumption calculated at S2 exceeds the threshold pTH, a temperature of the distal end portion 21 is presumed to exceed the threshold TH with the lapse of time as shown by the graph g3 in FIG. 4 to prevent the endoscope apparatus 1 from maintaining a predetermined performance level. Hence, at S4, a process to prevent a temperature rise in the distal end portion 21 or, for example, a process to stop power supply to the signal wires L and stop operation of the voice coil motor 32 serving as an actuator for a predetermined period is performed.

The control portion 40 thus makes a control to execute a predetermined process based on power consumption of the internal resistance R2 as calculated at S2 serving as a power consumption calculation part and the threshold pTH serving as power consumption threshold information.

The control portion 40 executes a predetermined process and then, after the lapse of a predetermined period, executes the processes shown in FIG. 6 again. It is thus possible to maintain or manage a temperature of the distal end portion 21 without exceeding the threshold TH.

As stated above, according to the aforementioned first embodiment, it is possible to provide an endoscope apparatus and a video processor in which a temperature of the distal end portion of the insertion portion can be maintained or managed without providing a temperature sensor inside the distal end portion.

As a result, because it is unnecessary to provide a temperature sensor inside the distal end portion of the insertion portion, it is possible to prevent the distal end portion from becoming larger.

Note that the predetermined process executed at S4 in the aforementioned example when power consumption of the internal resistance R2 exceeds the threshold pTH may also be executed in a stepwise manner once or several times before power consumption of the internal resistance R2 reaches the threshold pTH by setting a plurality of thresholds in advance. For example, when power consumption of the internal resistance R2 exceeds a threshold that is less than the threshold pTH, the control portion 40 may execute a predetermined process such as alternation to a drive mode with a smaller amount of heat generation to make a control to drive the image pickup device 34.

Further note that the control in the aforementioned example is set to prevent a temperature of the distal end portion 21 from reaching the threshold TH or above based on power consumption of the voice coil motor 32 on the assumption that a temperature of the distal end portion 21 is most affected by power consumption of the voice coil motor 32. Instead, a relationship between power consumption of each of other components inside the distal end portion 21 such as the image pickup portion 31, the LED 33 and the position detection sensor 33A and a temperature change in the distal end portion 21 may be obtained in advance through experiment or the like to maintain and manage a temperature of the distal end portion 21 by adjusting a temperature of each of other components with the use of information of the relationship between power consumption of each of other components and a temperature change in the distal end portion 21.

Second Embodiment

The first embodiment involves comparison between power consumption of the internal resistance R2 and the power consumption threshold pTH, whereas a second embodiment involves comparison between an integrated value of power consumption for a predetermined period and a power consumption integrated value threshold SpTH.

Components of an endoscope apparatus according to the second embodiment are substantially the same as the components of the endoscope apparatus 1 according to the first embodiment and therefore explanation is made only for different components while omitting explanation of the same constituent elements to which the same reference numbers are given.

According to the present embodiment, the aforementioned ratio information Rat and information of the integrated value threshold SpTH to be described later are stored in the memory 36 in advance.

Figure 7:
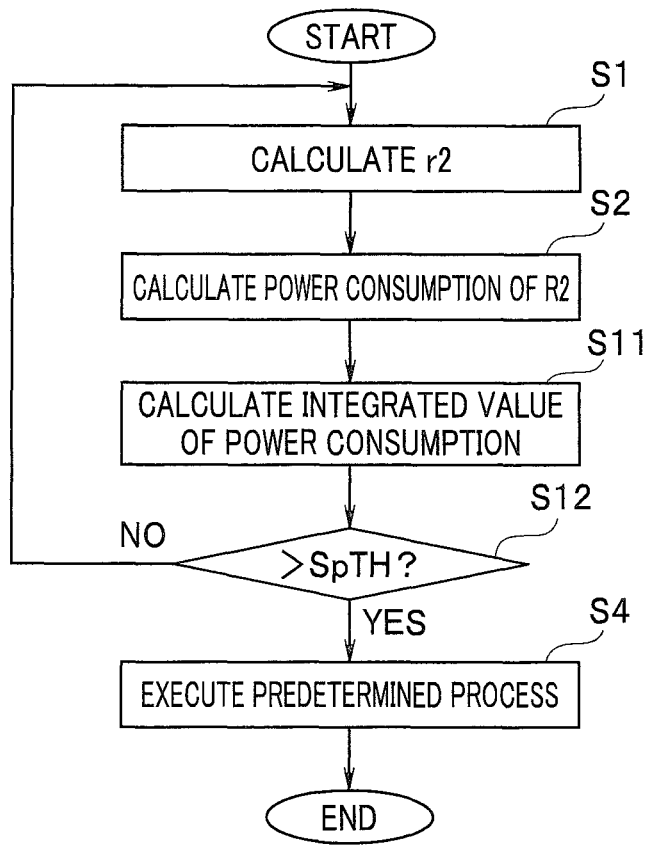
FIG. 7 is a flowchart showing an example of a flow of temperature maintenance processes in the distal end portion 21 of the endoscope apparatus 1 according to a second embodiment of the present invention.

FIG. 7 is a flowchart showing an example of a flow of temperature maintenance processes applied to the distal end portion 21 in the endoscope apparatus 1. A process program in FIG. 7 is stored in the ROM and read by the CPU in the control portion 40. The processes in FIG. 7 contain the same processes shown in FIG. 6 and therefore the same processes as the processes in FIG. 6 are provided with the same step numbers to simplify explanation.

The control portion 40 calculates the resistance value r2 of the internal resistance R2 of the voice coil motor 32 (S1), and calculates power consumption of the resistance value r2 of the internal resistance R2 of the voice coil motor 32 (S2). Power consumption of the resistance value r2 is calculated by using the aforementioned equations (1) to (6). A power consumption value calculated at S2 is temporarily stored for a predetermined period TT in the RAM of the control portion 40.

The control portion 40 calculates an integrated value of power consumption calculated during the predetermined period TT from a current point of time (S11). The predetermined period TT falls in a range of, for example, several minutes to several tens of minutes.

The control portion 40 then determines whether or not an integrated value of power consumption calculated at S11 exceeds the integrated value threshold SpTH read from the memory 36 (S12). Namely, an integrated value of power consumption for the predetermined period TT is calculated at S2 and S11. Power consumption threshold information SpTH is a value corresponding to the predetermined period TT.

If an integrated value of power consumption calculated at S1 does not exceed the integrated value threshold SpTH (S12: NO), the process returns to S1.

If an integrated value of power consumption calculated at S11 exceeds the integrated value threshold SpTH (S12: YES), the control portion 40 executes a predetermined process (S4).

Figure 8:
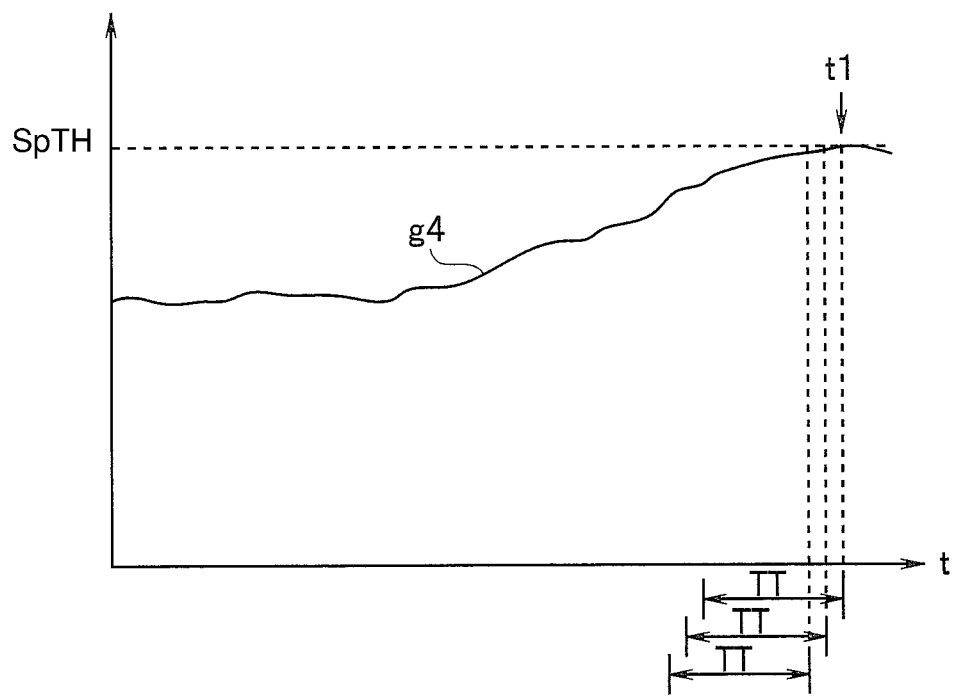
FIG. 8 provides a graph showing a change in an integrated value of power consumption according to the second embodiment of the present invention.

FIG. 8 provides a graph showing a change in an integrated value of power consumption PS.

In FIG. 8, a graph g4 indicates a change in an integrated value of power consumption PS of the internal resistance R2. An integrated value of power consumption PS varies as shown in FIG. 8. In FIG. 8, the integrated value threshold SpTH is a threshold of an integrated value of power consumption PS of the internal resistance R2. When an integrated value of power consumption PS of the internal resistance R2 exceeds the integrated value threshold SpTH, a temperature of the distal end portion 21 is presumed to exceed the threshold TH.

The integrated value threshold SpTH is determined through experiment or simulation and stored in the memory 36. The integrated value threshold SpTH is a value corresponding to an upper limit value of a temperature of the distal end portion 21 in which the endoscope apparatus 1 can maintain a predetermined performance level.

In the first embodiment, a temperature of the distal end portion 21 is presumed to exceed the threshold TH when a certain period of time elapses in the state where power consumption of the internal resistance R2 exceeds the threshold pTH. However, even if power consumption of the internal resistance R2 reaches the integrated value threshold SpTH for a moment, a temperature of the distal end portion 21 does not immediately reach the threshold TH. In other words, if power consumption of the internal resistance R2 increases temporarily and then decreases, a temperature of the distal end portion 21 does not reach the threshold TH or more.

Therefore, in the present embodiment, a temperature of the distal end portion 21 is presumed to reach the threshold TH or more when an integrated value of power consumption for the predetermined period TT exceeds the integrated value threshold SpTH.

In FIG. 8, an integrated value of power consumption PS exceeds the integrated value threshold SpTH at time t1 and the control portion 40 then executes a predetermined process such as a process to stop operation of the voice coil motor 32 for a predetermined period. The control portion 40 executes the predetermined process and then, after the lapse of a predetermined period, executes the processes in FIG. 7 again.

As stated above, according to the present embodiment, owing to the use of an integrated value of power consumption, a temperature of the distal end portion 21 can be maintained or managed while reflecting effects of a heat capacity of the distal end portion 21.

Thus, an effect similar to the effect of the first embodiment can also be obtained in the present embodiment.

Modifications of the aforementioned two embodiments are explained next.

Modification 1

In each of the aforementioned embodiments, the current value I of a current flowing through the two signal wires L and the voltage value V between the two signal wires L are detected to calculate power consumption of the internal resistance R2 with the use of the ratio information Rat stored in the memory 36. In the present modification 1, the current value I of a current flowing through the two signal wires L is detected to calculate power consumption of the internal resistance R2 with the use of the resistance value r2 of the internal resistance R2 stored in the memory 36 and the current value I.

Namely, from the current value I detected by the current sensor 52 serving as a signal detection portion and the resistance value r2 stored in the memory 36, power consumption of the internal resistance R2 is calculated.

Note that in place of the resistance value r2 of the internal resistance R2, information of the composite resistance value R and the resistance value r1 of the signal wires L may be stored in the memory 36 so as to calculate the resistance value r2 in the control portion 40 from the composite resistance value R and the resistance value r1.

The first embodiment involves calculation of the resistance value r2 of the internal resistance R2 while considering temperature characteristics of the internal resistance R2 in a use environment of the endoscope apparatus 1. The present modification 1 is applicable in the case where the resistance value r2 of the internal resistance R2 can be presumed to be constant in view of temperature characteristics.

Modification 2

In each of the aforementioned embodiments, the current value I of a current flowing through the two signal wires L and the voltage value V between the two signal wires L are detected to calculate power consumption of the internal resistance R2 with the use of the ratio information Rat stored in the memory 36. In the present modification 2, the voltage value V between the two signal wires L is detected to calculate power consumption of the resistance value r2 of the internal resistance R2 with the use of the composite resistance value R stored in the memory 36, the resistance value r2 of the internal resistance R2 and the voltage value V.

Namely, the voltage value V detected by the voltage sensor 53 serving as a signal detection portion and the composite resistance value R stored in the memory 36 are used to calculate the current value I of a current flowing through the two signal wires L, and the calculated current value I and the resistance value r2 stored in the memory 36 are used to calculate power consumption of the internal resistance R2.

Note that in place of the composite resistance value R and the resistance value r2, information of the composite resistance value R and the resistance value r1 of the signal wires L may be stored in the memory 36 to calculate the resistance value r2 from the composite resistance value R and the resistance value r1.

In the first embodiment, the resistance value r2 of the internal resistance R2 is calculated while considering temperature characteristics of the internal resistance R2 in a use environment of the endoscope apparatus 1. The present modification 2 is applicable in the case where the resistance value r1 of the conductor resistance R1 and the resistance value r2 of the internal resistance R2 can be both presumed to be constant in view of temperature characteristics.

Modification 3

In each of the aforementioned embodiments, power consumption of the internal resistance R2 serving as a point resistance in the voice coil motor 32 is calculated. However, if a resistance value of any of the signal wires L, soldering parts of the signal wires L and the coil of the voice coil motor 32 becomes larger due to a change with time, it hinders correct calculation of power consumption of the internal resistance R2 and there is a risk of preventing appropriate maintenance or management of a temperature of the distal end portion 21.

In the present modification, an allowable value is set in advance for the composite resistance value R and it is determined whether the composite resistance value R exceeds the allowable value or not. The allowable value is a value set in advance to allow correct calculation of power consumption. If the composite resistance value R exceeds the allowable value, the control portion 40 executes a predetermined process.

Figure 9:
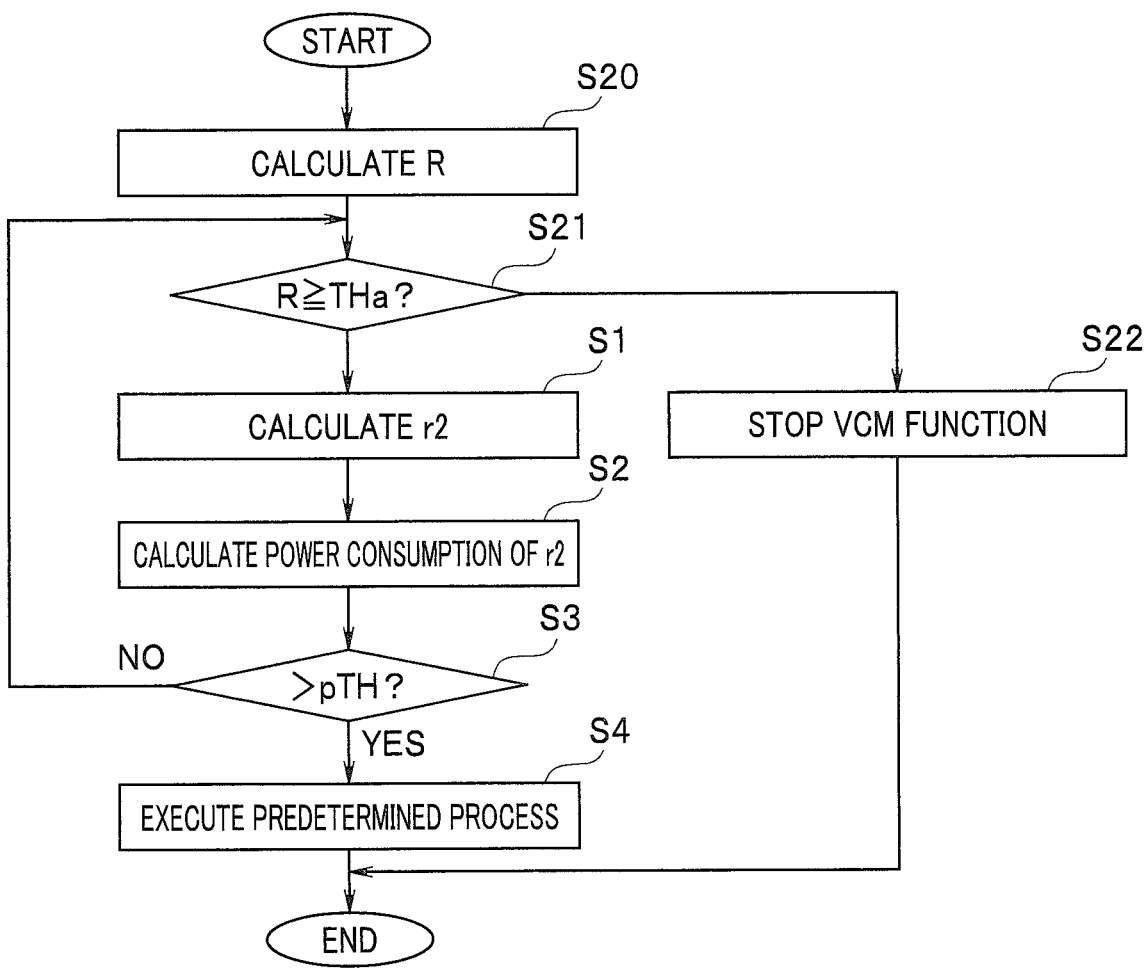
FIG. 9 is a flowchart showing an example of a flow of temperature maintenance processes in the distal end portion 21 of the endoscope apparatus 1 according to a modification 3.

FIG. 9 is a flowchart showing an example of a flow of temperature maintenance processes applied to the distal end portion 21 in the endoscope apparatus 1 according to the present modification 3. In FIG. 9, the same processes as the processes in FIG. 6 are provided with the same step numbers to simplify explanation.

Firstly, the control portion 40 calculates the composite resistance value R from the current value I and the voltage value V (S20). The control portion 40 then determines whether or not the composite resistance value R is the predetermined threshold THa or more (S21). The threshold THa is the aforementioned allowable value.

If the composite resistance value R is the predetermined threshold THa or more (S21: YES), the control portion 40 stops function of the voice coil motor 32 (S22). Namely, the voice coil motor 32 is brought into an unoperated state. After S22, no process is performed.

In other words, the process at S20 constitute a composite resistance detection part to detect the composite resistance value R of the resistance value r2 of the resistance component of the coil C and the resistance value r1 of the two signal wires L, and the control portion 40 does not execute a predetermined process when the composite resistance value R detected by the composite resistance detection part is a predetermined threshold THa or more.

If the composite resistance value R is less than the predetermined threshold THa (S21: NO), the control portion 40 executes the process at S1. The processes after S1 are as stated above.

According to the present modification 3, it is prevented to calculate inaccurate power consumption resulting from an increased resistance value of the signal wires L or the like due to a change with time of the signal wires L.

As stated above, according to the present modification 3, abnormality of the internal resistance R2 and the signal wires L can be detected and therefore a temperature of the distal end portion 21 can be maintained or managed more appropriately.

Note that in order to prevent calculation of inaccurate power consumption due to a change with time of other components such as the image pickup portion 31, the LED 33 and the position detection sensor 33A, a composite resistance value of each of other components may also be detected in the same manner as the case of the coil C to detect abnormality of an internal resistance and a signal wire of each of other components such as the image pickup portion 31.

For example, in the case of the above position detection sensor 33A, at least any one of a current supplied to signal wires of two sensors connected to both ends of the position detection sensor 33A and a voltage applied to the signal wires of the two sensors is detected. From the at least one value of the detected current and voltage and resistance value information of a resistance component of the position detection sensor 33A, power consumption of the position detection sensor 33A is calculated. Based on the calculated power consumption of the position detection sensor 33A and power consumption threshold information of the position detection sensor 33A, the control portion 40 executes a predetermined process. Then, a composite resistance value of a resistance value of the resistance component of the position detection sensor 33A and a resistance value of the signal wires of the two sensors is detected. When the composite resistance value of the position detection sensor 33A is a predetermined value or more, the control portion 40 makes a control to execute a predetermined process such as a process to stop operation of the position detection sensor 33A.

As stated above, according to each of the aforementioned embodiments and the modifications, it is possible to provide an endoscope apparatus and a video processor in which a temperature of the distal end portion of the insertion portion can be maintained and managed without providing a temperature sensor inside the distal end portion.

As a result, because it is unnecessary to provide a temperature sensor inside the distal end portion of the insertion portion, it is possible to prevent the distal end portion from becoming larger.

The present invention is not limited to the aforementioned embodiments and various changes and modifications, etc. can be made in the range without changing the gist of the present invention.

What is claimed is:

1. An endoscope apparatus comprising:
an endoscope;
a device provided in a distal end portion of an insertion portion of the endoscope and having a resistance component;
a signal wire inserted into the insertion portion and connected to both ends of the device; and
a processor comprising hardware, wherein the processor is configured to:
   detect at least one value of:
      a current supplied to the signal wire, and
      a voltage applied to the signal wire,
   calculate power consumption of the device from the at least one value detected and resistance value information of the resistance component, and
   stop power supply to the signal wire when the calculated power consumption of the device exceeds a power consumption threshold.

2. The endoscope apparatus according to claim 1, wherein the endoscope further comprises a memory configured to store the resistance value information of the resistance component.

3. The endoscope apparatus according to claim 1, wherein the endoscope further comprises a memory configured to store information of the power consumption threshold.

4. The endoscope apparatus according to claim 1, wherein the processor is configured to detect each of the value of the current supplied to the signal wire and the value of the voltage applied to the signal wire, and
the processor is configured to calculate the power consumption from the value of the current, the value of the voltage and a ratio of a resistance value of the device and a resistance value of the signal wire.

5. The endoscope apparatus according to claim 4, wherein the endoscope further comprises a memory configured to store information of the ratio, and
the processor is configured to use the information of the ratio read from the memory to calculate the power consumption.

6. The endoscope apparatus according to claim 1, wherein the processor is configured to detect the value of the current supplied to the signal wire, and
the processor is configured to calculate the power consumption from the value of the current and a resistance value of the device.

7. The endoscope apparatus according to claim 6, wherein the endoscope further comprises a memory configured to store resistance value information of the resistance value of the device, and
the processor is configured to use the resistance value information of the resistance value of the device stored in the memory to calculate the power consumption.

8. The endoscope apparatus according to claim 1, wherein the processor is configured to detect the value of the voltage applied to the signal wire, and
the processor is configured to calculate the power consumption based on the value of the voltage and a composite resistance value of a resistance value of the device and a resistance value of the signal wire.

9. The endoscope apparatus according to claim 8, wherein the endoscope further comprises a memory configured to store the resistance value of the device and resistance value information of the composite resistance value, and
the processor is configured to calculate the power consumption by using the resistance value of the device and the resistance value information of the composite resistance value stored in the memory.

10. The endoscope apparatus according to claim 1, wherein
the endoscope further comprises a memory configured to store model information of the endoscope, and
the processor is configured to obtain the resistance value information of the resistance component based on the model information and use the resistance value information obtained to calculate the power consumption.

11. The endoscope apparatus according to claim 1, wherein the power consumption of the device calculated in the processor is an integrated value of power consumption for a predetermined period, and the power consumption threshold is a value corresponding to the predetermined period.

12. The endoscope apparatus according to claim 11, wherein
the endoscope further comprises a memory configured to store information of the predetermined period, and
the processor is configured to calculate the power consumption by using the information of the predetermined period read from the memory.

13. The endoscope apparatus according to claim 1, wherein the processor is configured to detect a composite resistance value of a resistance value of the resistance component and a resistance value of the signal wire, and the processor is configured not to execute a predetermined process when the detected composite resistance value is a predetermined value or more.

14. The endoscope apparatus according to claim 13, wherein
the processor is configured to detect each of the value of the current supplied to the signal wire and the value of the voltage applied to the signal wire, and
the processor is configured to calculate the power consumption from the value of the current, the value of the voltage and a ratio of a resistance value of the device and the resistance value of the signal wire.

15. The endoscope apparatus according to claim 1, wherein
the endoscope is any endoscope selected from a plurality of endoscopes, and
the endoscope further comprises a memory configured to store the resistance value information of the resistance component.

16. The endoscope apparatus according to claim 1, wherein the device is included in an actuator provided in the distal end portion, and a predetermined process is a process to stop operation of the actuator.

17. The endoscope apparatus according to claim 16, wherein
the actuator is a voice coil motor configured to drive a zoom optical system provided in the distal end portion, and
the resistance component is a resistance component of a coil of the voice coil motor.

18. The endoscope apparatus according to claim 1, wherein the device is included in a sensor provided in the distal end portion, and a predetermined process is a process to stop operation of the sensor.

19. The endoscope apparatus according to claim 18, wherein the sensor is a sensor for position detection of a zoom lens provided in the distal end portion.

20. An image processing apparatus comprising:
a processor comprising hardware and allowing connection of an endoscope, wherein the processor the processor being configured to:
detect at least one value of:
a current supplied to a signal wire connected to both ends of a device provided in a distal end portion of an insertion portion of the endoscope and having a resistance component, and
a voltage applied to the signal wire,
calculate power consumption of the device from the at least one value detected and resistance value information of the resistance component, and
stop power supply to the signal wire when the calculated power consumption of the device exceeds a power consumption threshold.

* * * * *